(12) United States Patent
Sugano et al.

(10) Patent No.: US 7,375,247 B2
(45) Date of Patent: May 20, 2008

(54) METHOD FOR PRODUCING DEUTERATED METHYL METHACRYLATE

(75) Inventors: Yuichi Sugano, Niigata (JP); Takafumi Abe, Chigasaki (JP); Toshifumi Abe, Tsuchiura (JP)

(73) Assignee: Taiyo Nippon Sanso Corporation, Tokyo (JP)

( * ) Notice: Subject to any disclaimer, the term of this patent is extended or adjusted under 35 U.S.C. 154(b) by 0 days.

(21) Appl. No.: 10/569,643

(22) PCT Filed: Sep. 1, 2004

(86) PCT No.: PCT/JP2004/013000

§ 371 (c)(1),
(2), (4) Date: Feb. 27, 2006

(87) PCT Pub. No.: WO2005/023748

PCT Pub. Date: Mar. 17, 2005

(65) Prior Publication Data

US 2007/0043242 A1 Feb. 22, 2007

(30) Foreign Application Priority Data

Sep. 4, 2003 (JP) .............................. 2003-312743

(51) Int. Cl.
*C07C 67/20* (2006.01)
(52) U.S. Cl. .................................................... 560/215
(58) Field of Classification Search ................ 560/215
See application file for complete search history.

(56) References Cited

U.S. PATENT DOCUMENTS 4,138,194 A * 2/1979 Beasley et al. ............. 385/143
4,421,865 A 12/1983 Shen
4,645,856 A 2/1987 Herold

FOREIGN PATENT DOCUMENTS

| JP | 2004-10593 | 1/2004 |
|----|------------|--------|
| JP | 2004-10594 | 1/2004 |
| JP | 2004-10595 | 1/2004 |

OTHER PUBLICATIONS

Hermann D Noether The Journal of Chemical Physics vol. 10, Dec. 1942, No. 12 pp. 693-699.*
Hermann D Noether Infra-Red and Raman Spectra of Polyatomic Molecules The Journal of Chemical Physics vol. 10 Dec. 1942, No. 12.*
Nagai et al, "Infrared Spectra of Deuterated Poly(methyl methacrylates)", Journal of Polymer Science, 62(174). S95-S98 CODEN: JPSCAU; ISSN: 0022-3832, 1962, XP008070279; p. 95. J. Poly. Sci., vol. 62, S95 (1962).
Aida et al, "Living Polymerization . . . ", J. Phy. Org. Chem., vol. 8, p. 249 (1995).
Beersmans et al, "Synthese et etude . . . ", Bull. Soc. Chim. Belg., 56 (1947) 81, abstract.
Noether, "Infra-Red and Rama Spectra . . . ", J. Chem. Phys., 10 (1942) 694.

* cited by examiner

*Primary Examiner*—Yvonne Eyler
*Assistant Examiner*—Lalitha Nagubandi
(74) *Attorney, Agent, or Firm*—Nixon & Vanderhye P.C.

(57) ABSTRACT

A method for producing MMA-$d_8$ which includes a step of exchanging D in hydroxyl group of methanol-$d_4$ represented by the formula: $CD_3OD$ with H to prepare the methanol-$d_3$ represented by the formula $CD_3OH$ and simultaneously recovering a deuterium-containing compound, and a step of reacting methanol-$d_3$ with sulfuric acid salt of methacrylic acid amide represented by the formula $CD_2=(CD_3)CO(NH_2 \cdot H_2SO_4)$ to prepare MMA-$d_8$ represented by the formula: $CD_2=(CD_3)COOCD_3$.

10 Claims, 2 Drawing Sheets

METHOD FOR PRODUCING DEUTERATED METHYL METHACRYLATE

This application claims benefit of JP 2003-312743 filed 4 Sep. 2003, the entire content of which is hereby incorporated by reference.

BACKGROUND OF THE INVENTION

1. Field of the Invention

Priority is claimed on Japanese Patent Application No. 2003-312743, filed Sep. 4, 2003, the content of which is incorporated herein by reference.

The present invention relates to an excellent method in terms of utilization efficiency of deuterium atoms for producing deuterated methyl methacrylate-$d_8$ represented by the formula $CD_2=C(CD_3)COOCD_3$ (D represents a deuterium atoms), which is hereinafter referred to as MMA-$d_8$ sometimes, from acetone-$d_6$, $(CD_3)_2CO$, and methanol-$d_4$, hereinafter sometimes referred to as $CD_3OD$. MMA-$d_8$ is a long-awaited compound as a raw material for plastic optical fibers and optical waveguide materials having low transmission loss.

2. Description of the Related Art

Plastic optical fibers are essential for large capacity communication networks installed in houses and offices and are a functional medium having a combination of low losses and large bandwidth of quartz optical fibers and tractability of copper wires. A polymer optical wave guide which has a large thermooptical effect and is easy to process is a long-awaited material in constructing optical communication devices such as optical waveguides instead of conventional glass or inorganic crystal materials.

An inexpensive and processable polymethylmethacrylic acid (PMMA) heretofore has often been used as a material for polymer optical communication. PMMA is mainly used in visible wavelength regions because of high absorption loss of the optical signal due to carbon-hydrogen bonding at wavelengths in the near-infrared region which is used for the optical signal, however, transmission loss is also high at visible wavelength regions since the overtone of near-infrared absorption appears in the near-infrared region. Deuterated PMMA in which hydrogens are replaced by deuterium atoms has been developed to solve this problem. Deuterated PMMA makes it possible to form a material for optical communication having low transmission loss due to a shift to the long-wavelength side of near-infrared absorption.

MMA-$d_8$, which is a raw material of deuterated PMMA, may be prepared by applying the acetone cyanohydrin method (ACH method), generally. In this method, methylmethacrylate-$d_8$ is prepared by synthesizing deuterated acetone cyanohydrin from acetone-$d_6$ and hydrocyanic acid or deuterated hydrocyanic acid, reacting with sulfuric acid or deuterated sulfuric acid, and esterifying of methanol-$d_4$ or methanol-$d_3$, hereinafter referred to as $CD_3OH$, the methyl group of which is fully deuterated (see documents 1 and 2).

Acetone-$d_6$ as a raw material is prepared by reacting acetone and deuterated water under the presence of potassium carbonate or reacting acetone and deuterated water under the presence of sulfuric acid. On the other hand, deuterated methanol and methanol-$d_4$ are prepared by reacting deuterium and carbon monoxide in the same way methanol method is normally synthesized. $CD_3OH$ is produced by bringing methanol-$d_4$ into contact with a large quantity of water is nor, for example, refer documents 3 and 4.

As described above, methanol-$d_4$ is easier to synthesize and acquire as deuterated methanol than methanol-$d_3$. When methylmethacrylate-$d_8$ is synthesized by the conventional ACH method using methanol-$d_4$ and acetone-$d_6$ as a raw material, reacting acetone-$d_6$ with normal hydrocyanic acid to produce acetone cyanohydrin-$d_6$, further treating with normal non-deuterated sulfuric acid, and reacting with methanol-$d_4$, 2 atoms of deuterium atom is mixed into waste sulfuric acid water and waste ammonium sulfate. A great amount of work is needed for recovering these deuterated atoms from these waste, expensive deuterated atoms would be loss in large quantity when waste, and a large amount of energy loss occurs when recover, thereby production costs increase.

Document 1: J. Poly. Sci., vol. 62, S95 (1962)
Document 2: J. Phy. Org. Chem. vol. 8, P249 (1995)
Document 3: Bull. Soc. Chim. Belg., 56 (1947) 81
Document 4: J. chem. Phys., 10 (1942) 694

SUMMARY OF THE INVENTION

A purpose of the present invention is to provide an industrially available manufacturing method for producing highly-pure MMA-$d_8$ with good efficiency using acetone-$d_6$ and methanol-$d_4$ both which are fully deuterated of hydrogens in molecules and are economic and easy-obtainable as a synthetic raw material while recovering and using a compound including expensive deuterium atoms being by-produced in a reaction process while keeping both a chemical purity and a deuteration rate which is useful as a plastic raw material for plastic optical fibers, though using a recovered compound.

The present inventors keenly examined a method for producing MMA-$d_8$ while effectively circulating expensive deuterium atoms to solve the above problems and found a method for producing MMA-$d_8$ from acetone-$d_6$ and methanol-$d_4$ as starting materials, preparing $CD_3OH$ from methanol-$d_4$, preparing MMA-$d_8$ from acetone cyanohydrin-$d_6$ produced by the obtained $CD_3OH$ and acetone-$d_6$ while reutilizing a deuterium-containing compound which are recovered in producing $CD_3OH$ from methanol-$d_3$ as a part of raw materials for producing methanol-$d_4$ or acetone-$d_6$, thus completing the present invention.

The present method relates to the excellent use efficiency of deuterium atoms method for producing MMA-$d_8$ showing from following (1) to (10).

(1) A method for producing MMA-$d_8$ comprising steps below;
  i) a step of preparing methanol-$d_3$ represented by the formula: $CD_3OH$ exchanging D to H in a hydroxyl group of methanol-$d_4$ represented by the formula: $CD_3OD$ and simultaneously recovering a deuterium-containing compound, and
  ii) a step of reacting above $CD_3OH$ with sulfuric acid salt of methacrylic acid amide represented by the formula $CD_2=C(CD_3)CO(NH_2.H_2SO_4)$ to prepare MMA-$d_3$ represented by the formula: $CD_2=C(CD_3)COOCD_3$.

(2) A method for producing MMA-$d_8$ according to above (1) further comprising a step of preparing $CD_3OD$ or acetone-$d_6$ represented by the formula: $(CD_3)_2CO$ from the above recovered the deuterium-containing compound as a raw material.

(3) A method for producing MMA-$d_8$ according to above (1), reacting acetone-$d_6$ and normal hydrocyanic acid to prepare acetone cyanohydrin-$d_6$, further treating this with normal non-deuterated sulfuric acid, and then reacting this with $CD_3OH$.

(4) A method for producing MMA-$d_8$ according to above (1) comprising a step of contacting methanol-$d_4$ and normal water to prepare $CD_3OH$.

(5) A method for producing MMA-$d_8$ according to above (4) in which the deuterium-containing compound recovered in preparing $CD_3OH$ by contacting methanol-$d_4$ with normal water is deuterated water.

(6) A method for producing MMA-$d_8$ according to above (1) including a method to prepare $CD_3OH$, reacting methanol-$d_4$ with an acid compound to prepare acid methyl-ester-$d_3$ which methyl groups are fully deuterated, hydrolyzing acid obtained methyl-$d_3$-ester which methyl groups are fully deuterated with normal water to prepare $CD_3OH$ and the acid compound.

(7) A method for producing MMA-$d_8$ according to above (6) in which the deuterium-containing compound recovered in preparing acid methyl-$d_3$-ester which methyl group is fully deuterated by reacting methanol-$d_4$ with the acid compound is a deuterium atom.

(8) A method for producing MMA-$d_8$ according to above (6) reutilizing the acid compound recovered in hydrolyzing acid methyl-$d_3$-ester which methyl group is fully deuterated with normal water to prepare $CD_3OH$ and the acid compound as esterification agent of methanol-$d_4$.

(9) A method for producing MMA-$d_8$ according to above (1) including a step to prepare $CD_3OH$, reacting methanol-$d_4$ with metal to prepare metal methoxide-$d_3$ which methyl group is fully deuterated and hydrolyzing the obtained metal methoxide-$d_3$ which methyl group is fully deuterated with normal water to prepare $CD_3OH$ and metal hydroxide.

(10) A method for producing MMA-$d_8$ according to above (9) in which the deuterium-containing compound recovered in preparing metal methoxide-$d_3$ which methyl group is fully deuterated by reacting methanol-$d_4$ with metal is a deuterium atom.

(11) A method for producing MMA-$d_8$ according to above (3) reutilizing as a part of raw materials for producing methanol-$d_4$ and acetone-$d_6$, a mixture including normal water and deuterated water recovered in treating acetone cyanohydrin-$d_6$ with normal non-deuterated sulfuric acid and then reacting with $CD_3OH$ to produce MMA-$d_8$.

According to the present invention, it is possible to produce effectively the promising MMA-$d_8$ as a raw material for plastic optical fibers and optical waveguide materials having low transmission loss from acetone-$d_6$ and methanol-$d_4$ as starting materials while circulating expensive deuterium atoms being by-produced in a reaction process and this have great significance industrially.

DETAILED DESCRIPTION OF THE INVENTION

Figure 1:
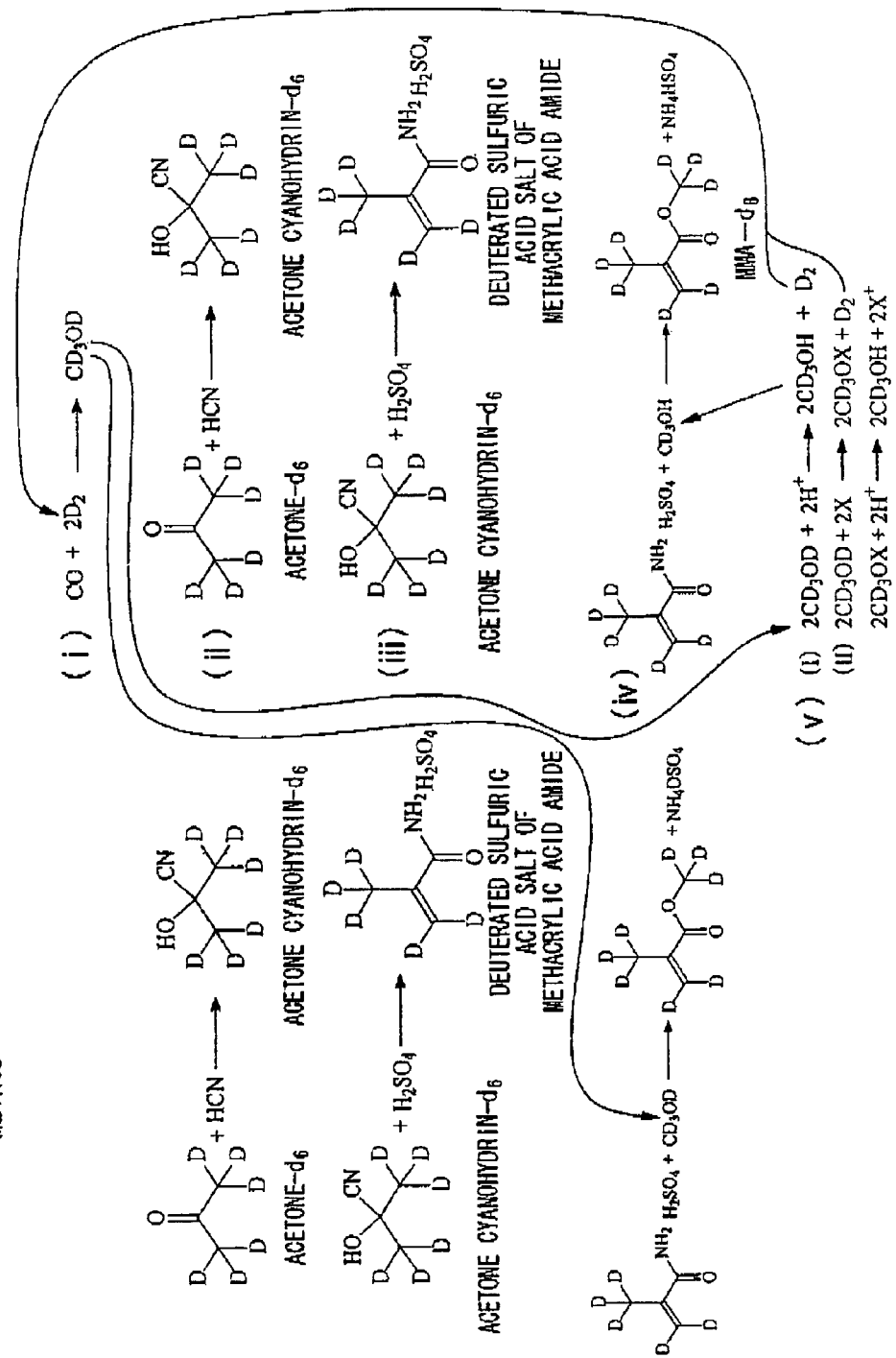
FIG. 1 shows reaction formulas of the conventional method and the present invention method.

A more detailed description of the present invention method follows. The reaction formulas of the conventional method and the present invention method showed in FIG. 1 is referred.

First, methanol-$d_4$ is made to be $CD_3OH$. This process is shown as formula (v) in FIG. 1. As this process, the methods from following (1) to (3) are exemplified. Meanwhile, methanol-$d_4$ which is produced from carbon monoxide and deuterium atom generally, as shown in formula (i) in FIG. 1 and which is deuterated at 99.8% or more deuteration ratio is easily available.

(1) A method reacting methanol-$d_4$ with water.

(2) A method reacting methanol-$d_4$ with the acid compound to prepare methyl-$d_3$-ester which methyl group is fully deuterated and hydrolyzing obtained acid methyl-$d_3$-ester which methyl group is fully deuterated with normal water to prepare $CD_3OH$ and the acid compound.

(3) A method reacting methanol-$d_4$ with metal to prepare metal methoxide-$d_3$ which methyl group is fully deuterated and hydrolyzing the obtained metal methoxide-$d_3$ which methyl groups are fully deuterated with normal water to prepare $CD_3OH$ and metal hydroxide.

The above (1) method is explained as follows. $CD_3OH$ is prepared from methanol-$d_4$ and water. Water including deuterium atom is recovered since it is by-produced at that time. The recovered water including deuterium atom can be provided as a raw material for producing deuterated water. Acetone-$d_6$ can be prepared by reflux with the obtained deuterated water with acetone under a basic condition. On the other hand, methanol-$d_4$ can be produced by deuterium as a raw material which is prepared by electrolysis of deuterated water. Generally, when preparing $CD_3OH$ from water and methanol-$d_4$, a large quantity of water is needed since deuterium concentration depends on the equilibrium of H-D in the system and the concentration of deuterium atom in water becomes low, however, $CD_3OH$ can be recovered with the original isotope enrichment.

Above (2) method is explained as follows. In this method, methyl-$d_3$-ester and deuterated water is prepared by reacting the acid compound and methanol-$d_4$. In this case, using gas phase reaction which has advantage on the equilibrium for ester formation especially, it makes possible to increase the deuterium concentration in water. $CD_3OH$ and the acid are prepared from obtained methyl-$d_3$-ester and normal water and the recovered acid is reacted with methanol-$d_4$ again, thereby $CD_3OH$ is prepared effectively from water and methanol-$d_4$ catalyzed by the acid. As the acid in this method, normal organic carboxylic acids such as formic acid, acetic acid, propionic acid, isobutyric acid, and butyric acid; phosphoric acid and sulfuric acid or the like may be used.

Above (3) method is explained as follows. In this method, metal and methanol-$d_4$ are reacted, metal methoxide and deuterium are prepared, and then $CD_3OH$ and metal hydroxide is prepared from obtained metal methoxide and normal water. From this method, $CD_3OH$ is prepared effectively from metal, water, and methanol-$d_4$. As the metal in this method, alkali metals such as lithium, sodium, and potassium; alkali earth metals such as magnesium and calcium or the like may be used.

Next, using $CD_3OH$ obtained as described above, MMA-$d_8$ is prepared by esterification of deuterated sulfuric acid salt of methacrylic acid amide. This process is shown as formula (iv) in FIG. 1. In this esterification, $CD_3OH$ may be used 1 to 10 times more in mole than deuterated sulfuric acid salt of methacrylic acid amide. Since $CD_3OH$ is expensive, it is preferably to use 1 to 3 times more in mole to deuterated sulfuric acid salt of methacrylic acid amide. The excess $CD_3OH$ can be recovered by normal separation operation such as distillation or extraction after reaction and this can be reutilized. Ordinarily, the reaction is operated under reflux condition; however, it may be operated under pressurized condition to promote the esterification reaction by increasing the reflux temperature. In the esterfication of deuterated sulfuric acid salt of methacrylic acid amide, water as the reaction accelerator may be used. 0.0001-3 times mol of the water supplementation amount to deuterated sulfuric acid salt of methacrylic acid amide is preferable.

The reaction mixture containing the MMA-$d_8$ obtained as described above may be refined by the normal method. When the distillation method was used, for example, the reaction mixture is distillated by heating. In that case, it is preferable to distill under reduced pressure to avoid the side reaction such as the polymerization, the isotope exchange or the like caused by high temperature. To use the steam distillation is also possible. It is possible to refine 99.9% or more in chemical purity using the distillate obtained by the above operation and conduct a unit operation such as the normal distillation, extraction or the like. The constituent recovered in the distillate includes water containing deuterium atom. This may be supplied as a raw material of deuterated water production, also.

As described above, the deuterated water or the deuterium obtained from any processes can be re-used as raw materials of acetone-$d_6$ or methanol-$d_4$.

Next, a specific example of the production method of above deuterated sulfuric acid salt of methacrylic acid amide will be shown. In this method, acetone-$d_6$, methanol-$d_4$ hydrocyanic acid, and sulfuric acid are the starting material.

In this method, first, acetone cyanohydrin-$d_6$ is synthesized from acetone-$d_6$ and normal non-deuterated hydrocyanic acid. This reaction is shown as formula (ii) in FIG. 1. Acetone-$d_6$ having 99.8% or more deuteration rate is available on the market and may readily be used. Hydrocyanic acid which has low impurities and high chemical purity is preferable due to the smooth progress of the reaction.

Above reaction is equilibrium reaction adding hydrocyanic acid to carbonyl group described in Kirk-Othmer, Encyclopedia of Chemical Technology Third Edition, vol. 7, P385-P396. Lower reaction temperature is preferable since the equilibrium is lean to cyanohydrin side at low temperature and the isotope exchange is prevented. The reaction temperature is preferable from −20 to 30° C. In case that the reaction temperature is lower than −20° C., reaction rate would not be sufficient and hydrocyanic acid could solidify then such temperature is not preferable. In case that the reaction temperature is 30° C. or more, the reaction would have disadvantage in the view of equilibration and it could be easy to color due to the polymerization of hydrocyanic acid then such temperature is not preferable. When both substances are mixed, it is preferable that hydrocyanic acid is supplied gradually into acetone-$d_6$ added by catalyst in advance. From this operation, increase of the hydrocyanic acid concentration in the reaction mixture can be suppressed, thereby it is possible to suppress the isotope exchange occurred during the reaction. This method is preferable since the reaction temperature can be kept stable and the isotope exchange or the polymerization of hydrocyanic acid can be suppressed due to the control of the drastic exothermic heat. The reaction pressure may be any one of reduced pressure, ordinary pressure, and increased pressure. In the reaction, the catalyst may be generally, ammonia, amines such as trimethylamine, triethylamine, diethylamine; alkali metal compounds such as sodium hydroxide, potassium hydroxide, sodium cyanide, potassium cyanide, sodium carbonate, potassium carbonate; alkali earth metal compounds such as calcium hydroxide, basic ion-exchange resins, and basic compounds such as zeolite. Amines and alkali metal compounds are preferable in terms of easy handling and reaction rate. Minimum catalyst supplementation amount which progress the reaction is preferable and 0.00001-1 weight % is preferable.

The generated acetone cyanohydrin-$d_6$ is unstable and stabilized by adding the acid such as sulfuric acid. When sulfuric acid is added, for example, inexpensive normal non-deuterated sulfuric acid may be used. Unreacted constituent may or may not be distilled off, however, the following reactions after this has advantage by distilling off. When the unreacted constituent is distilled off, it is preferable to distill at 40° C. or less under reduced pressure in order to suppress the degradation of cyanohydrin.

Next, the dehydration and amidation is accomplished by dropping the above acetone cyanohydrin-$d_6$ to the normal non-deuterated sulfuric acid, and heating and stirring to generate sulfuric acid salt of deuterated methacrylic acid amide ($CD_2=C(CD_3)CONH_2 \cdot H_2SO_4$). This process is shown as formula (iii) in FIG. 1.

In this method, sulfuric acid is used normally 1-3 times more in mol than acetone cyanohydrin-$d_6$. Acetone cyanohydrin-$d_6$ is added dropwise at 40° C.-80° C. normally and the reaction is completed by further increasing the temperature at 110-160° C. after finishing dropping. In case that the dropping temperature is too low, the stirring would be insufficient due to the solidification of the reaction liquid. In case that the temperature after increasing is too low, the dehydration would be insufficient. In case that the temperature at dropping and after increasing the temperature is too high from the above temperature range, the yield would lower as well as the isotope exchange would be occurred at the unsaturated bond of methacryl group and such temperature is not preferable.

$CD_3OH$, or $CD_3OH$ including water is supplied to the obtained deuterated sulfuric acid salt of methacrylic acid amide thereby MMA-$d_8$ is obtained.

Next, one example of the device practicing the present invention method will be explained.

This device comprises: a catalyst column synthesizing $CD_3OD$; each feed pipe introducing CO and $D_2$ into this catalyst column; a reactor (I) which have a inlet for metal and water and synthesize $CD_3OH$ from $CD_3OD$; a $CD_3OD$ feed pipe introducing $CD_3OD$ synthesized in the above catalyst column into the above reactor (I); a reservoir storing the $D_2$ generated from the above reactor (I); a channel sending $D_2$ generated from the reactor (I) to the reservoir; a $D_2$ circulation pipe sending $D_2$ of the reservoir to the above catalyst column; a MMA-$d_8$ reactor having a inlet of methacrylic acid amide or the synthetic raw material thereof; a $CD_3OH$ transport pipe sending $CD_3OH$ generated in the reactor (I) to a reactor (II).

The above reactor (I) preferably includes a heater. From this, the generated liquid $CD_3OH$ would vaporize and be sent to the reactor (II).

The above reactor (II) preferably includes a heater. From this, the generated liquid MMA-$d_8$ would be sent outside of the reactor (II), for example, to a MMA-$d_8$ product tank.

The above $CD_3OD$ feed pipe preferably includes a cooling system along the path. From this, liquid $CD_3OD$ would be introduced into the reactor (I).

The $CD_3OH$ transport pipe sending $CD_3OH$ generated in the above reactor (I) to the reactor (II) preferably includes a rectification device (II) along the path. From this, $CD_3OH$ of high purity would be sent to the reactor (II).

The above rectification device (I) and (II) may be united partially. In that case, the device becomes simple and cost-effective.

The $CD_3OH$ transport pipe sending $CD_3OH$ generated in the above reactor (I) to the reactor (II) preferably includes a cooling system along the path. From this, $CD_3OH$ would be condensed and introduced into the reactor (II).

In the above MMA-$d_8$ reactor (II), sulfuric acid salt of methacrylic acid amide might be synthesized. In that case, the inlet of the above sulfuric acid salt of methacrylic acid amide may be the inlet of the synthetic raw materials thereof, for example, sulfuric acid, acetone cyanohydrin-$d_6$ or the like.

Figure 2:
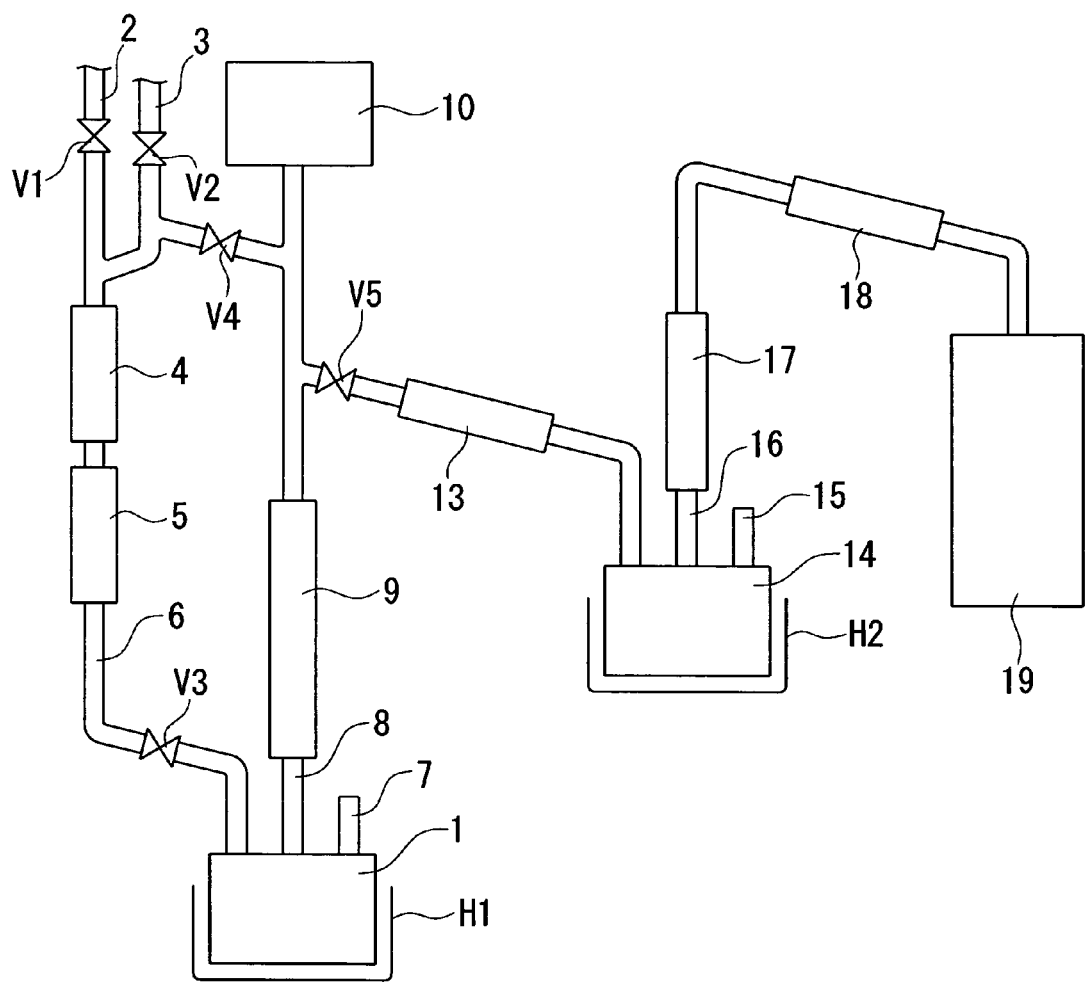
FIG. 2 is a schematic diagram of a device for implementing an example of the present invention method.

The above device is specifically explained using FIG. 2. In FIG. 2, symbols are represented below. 1 represents a $CD_3OH$ synthetic reactor (I); 2 represents a CO introduction pipe introducing CO to a catalyst column; 3 represents a $D_2$ introduction pipe introducing $D_2$ to a catalyst column; 4 represents a catalyst column filled with catalyst which synthesize $CD_3OD$ from CO and $D_2$; 5 represents a cooling system of gas $CD_3OD$ coming over the catalyst column; 6 represents a $CD_3OD$ introduction pipe introducing the above $CD_3OD$ to the reactor (I); 7 represents a feed port of metal and water feeding metal and water into the reactor (I) in order to transform from $CD_3OD$ to $CD_3OH$ in this reactor; 8 represents a rectification column refining $D_2$ and $CD_3OH$ generated in the reactor (I); 10 represents a $D_2$ reservoir; 11 represents a circulation pipe sending $D_2$ from the $D_2$ reservoir to the catalyst column; 12 represents a $CD_3OH$ transport pipe; 13 represents a $CD_3OH$ condenser tube; 14 represents a MMA-$d_8$ synthetic reactor (II); 15 represents a feed port of sulfuric acid salt of methacrylic acid amide into the reactor (II); 16 represents an MMA-$d_8$ outgoing pipe sending MMA-$d_8$ from the reactor (II); 17 represents a rectification column refining MMA-$d_8$ coming from the reactor (II); 18 represents a cooling system which cools and condenses the refined MMA-$d_8$; 19 represents a MMA-$d_8$ production tank; V1-V5 represents valves; H1 and H2 represents heaters.

Next, the process from the synthesis of $CD_3OD$ to obtain MMA-$d_8$ using this device is explained.

(1) V1 open, V2 open, V3 open, V4 close, V5 close; introducing carbon monoxide from the CO introduction pipe 2 and deuterium gas from the $D_2$ introduction pipe 3 respectively, preparing methanol-$d_4$ by passing through the catalyst column 4, condensing at the condenser tube 5, and introducing the reactor (I) 1.

(2) V1 close, V2 close, V3 close, V4 close, V5 close; feeding metal sodium from the feed port for metal and water 7 to the reactor (I), reacting with methanol-$d_4$, generating sodium methoxide-$d_3$ and deuterium gas, and storing the generated deuterium gas to the reservoir 10.

(3) V1 close, V2 close, V3 close, V4 close, V5 close; feeding water from the feed port for metal and water 7 to the reactor (I), reacting with sodium methoxide-$d_3$, and generating $CD_3OH$.

(4) V1 close, V2 close, V3 close, V4 close, V5 open; heating the reactor (I) by the heater H1, distilling $CD_3OH$, cooling to condense by the condenser tube 13, and introducing to the reactor (II) 14.

(5) V1 close, V2 close, V3 close, V4 close, V5 close; introducing sulfuric acid salt of methacrylic acid amide from the feed port of sulfuric acid salt of methacrylic acid amide 16, to the reactor (II), reacting with $CD_3OH$, and generating MMA-$d_8$.

(6) V1 close, V2 close, V3 close, V4 close, V5 close; heating the reactor (II) by heater H2, distilling MMA-$d_8$, introducing MMA-$d_8$ through the outgoing pipe sending MMA-$d_8$ 16, the rectification column refining MMA-$d_8$ 17, and the cooling system of MMA-$d_8$ 18 to the MMA-$d_8$ production tank 19.

(7) V1 open, V2 close, V3 close, V4 open, V5 close; introducing carbon monoxide from the CO introduction pipe 2 and $D_2O$ gas from reservoir 10, respectively, preparing methanol-$d_4$ by passing through the catalyst column 4, condensing at the condenser tube 5, and introducing into the reactor (I).

EXAMPLES

While preferred embodiments of the present invention are described below based on the Examples, it should be understood that these are exemplary of the invention and are not to be considered as being limited by the foregoing description.

In the following description, the deuteration rate is measured by the 1H-NMR internal reference method and the definition follows as shown below.

(1) Deuteration rate (%)=[1−{(the number of hydrogen atoms in generated deuterated methylmethacrylate)/(the number of hydrogen atoms in generated deuterated methylmethacrylate+the number of deuterium atoms)}]×100

(2) Deuteration rate of each bonding (%)=[1−{(the number of hydrogen atoms in each C-D bonding)/(the number of hydrogen atoms in each C-D bonding+the number of deuterium atoms)}]×100

Example 1

(1) Synthesis of $CD_3OH$:

1 mol of methanol-$d_4$ (deuteration rate 99.9%) and 10 mol of water were mixed and $CD_3OH$ was isolated by distillation. This mixing and distillation operation was repeated 4 times and 0.99 mol of $CD_3OH$ was obtained. Simultaneously, the water including deuterium atoms were recovered and 0.45 mol of deuterated water was obtained by the isotope enrichment.

(2) Synthesis of acetone-$d_6$ using the recovered deuterated water:

0.045 mol of acetone was mixed with 0.45 mol of deuterated water obtained by the previous step, 0.0001 mol of potassium carbonate anhydrous was added, and then acetone was isolated by distillation. This mixing-distillation operation was repeated 4 times and 0.04 mol of acetone-$d_6$ was obtained. The used deuterated water and potassium carbonate in the operation may be reutilized to the next mixing-distillation operation.

(3) Synthesis of acetone cyanohydrin-$d_6$:

0.333 mol of hydrocyanic acid was gradually supplied to a mixture of 0.333 mol of acetone-$d_6$ (deuteration rate 99.9%) and 0.0005 mol of triethylamine as a catalyst at 0° C. After the supply, the mixture was stirred for 4 hours at 1° C. and stabilized by adding 0.0004 mol of sulfuric acid, then transparent and colorless acetone cyanohydrin-$d_6$ was obtained at 96.5% yield.

(4) Generation of deuterated sulfuric acid salt of methacrylic acid amide and synthesis of MMA-$d_8$:

0.32 mol of acetone cyanohydrin-$d_6$ obtained the above was added dropwise into 0.48 mol of sulfuric acid at 70° C. After stirring for 1 hour at 75-80° C., it was heated to 140° C. and was kept for 30 minutes at the same temperature, and deuterated sulfuric acid salt of methacrylic acid amide was generated. After that, it was cooled to 115° C. and the mixture solution of 0.64 mol of $CD_3OH$ obtained the above and 0.48 mol water was added dropwise, and it was refluxed for 4 hours. A polymerization inhibitor was added into the distillate, and then the reaction mixture was distilled by steam distillation. Hexane was added to the reaction liquid, $CD_3OH$ was distilled off by fractional distillation, the distillation was continued until 0.25 mol of MMA-$d_8$ with chemical purity of or with over 99.9% was obtained. The deuteration rate of the product was measured and the deuteration rate of each position was as follows; that of C—$CD_3$ position was 99.2%, that of C=$CD_2$ position was 99.6%, that of O—$CD_3$ was 99.9%, and total deuteration rate was 99.6%. The above distillate included water contained deuterium atoms and it was possible to recover this to use as a raw material for deuterated water production.

Example 2

(1) Synthesis of $CD_3OH$:

5 g of proton Y-type zeolite which was crushed into 1-2 mm mesh as catalyst was filled into a glass flow tube reactor. The raw material liquid composed with 2 mol of methanol-$d_4$ (deuteration rate 99.9%) and 1 mol of isobutyric acid was supplied into the catalyst layer heated at 180° C. at the flow rate of 5 g/hr and the gas-phase catalytic reaction was accomplished, thereby methyl-$d_3$ isobutyrate was obtained at 90% yield. The unreacted raw material and the water containing deuterium atoms as a by-product were recovered by distillation, respectively. The unreacted isobutyric acid and methanol-$d_4$ may be supplied as reaction raw materials again, on the other hand, 0.45 mol of deuterated water was obtained from water including deuterium atoms by the isotope enrichment.

2 mol of water was supplied to 0.9 mol of obtained methyl-$d_3$ isobutyrate, the reaction-distillation using 10 cc of strong acid ion exchange resin catalyst was operated thereby $CD_3OH$ was obtained at 99% yield. The obtained isobutyric acid was recovered by the distillation and may be re-supplied as a raw material of methyl-$d_3$ isobutyrate production.

(2) Synthesis of acetone-$d_6$ using recovered deuterated water: the same as that of Example 1.

(3) Synthesis of acetone cyanohydrin-$d_6$: the same as that of Example 1.

(4) Generation of deuterated sulfuric acid salt of methacrylic acid amide and synthesis of MMA-$d_8$: the same as that of Example 1.

Example 3

(1) Synthesis of $CD_3OH$:

1 mol of methanol-$d_4$ (deuteration rate 99.9%) was charged into a 100 ml three-neck flask with a dropping funnel and a gas outlet, 1 mol of metal sodium was added, and the flask was evacuated. Methanol-$d_4$ was added dropwise from the dropping funnel and 0.45 mol of deuterated gas was recovered. On the other hand, the obtained sodium methoxide-$d_3$ was mixed with water, thereby the mixture of sodium hydroxide, $CD_3OH$ and water was obtained. 0.95 mol of $CD_3OH$ was prepared by distilling the mixture. The recovered deuterium gas was supplied to the synthesis of methanol-$d_4$.

(2) Synthesis of acetone cyanohydrin-$d_6$: the same as that of Example 1.

(3) Generation of deuterated sulfuric acid salt of methacrylic acid amide and synthesis of MMA-$d_8$: the same as that of Example 1.

What is claimed is:

1. A method for producing MMA-$d_8$ represented by the formula: $CD_2$=$C(CD_3)COOCD_3$, the method comprising;
   (i) preparing methanol-$d_3$ represented by the formula: $CD_3OH$ by exchanging D to H in a hydroxyl group of methanol-$d_4$ represented by the formula: $CD_3OD$,
   (ii) reacting acetone-$d_6$ and normal hydrocyanic acid to prepare acetone cyanohydrin-$d_6$, and treating the acetone cyanohydrin-$d_6$ by normal non-deuterated sulfuric acid to obtain a sulfuric acid salt of deuterated methacrylic acid amide represented by the formula $CD_2$=$C(CD_3)CO(NH_2.H_2SO_4)$,
   (iii) reacting the $CD_3OH$ with the sulfuric acid salt of deuterated methacrylic acid amide to prepare MMA-$d_8$ represented by the formula: $CD_2$=$C(CD_3)COOCD_3$, and
   (iv) recovering a deuterium-containing compound generated as a by-product in at least one of steps (i) and (iii), and
   reutilizing the recovered deuterium-containing compound as at least part of raw materials used for producing at least one of methanol-$d_4$ or acetone-$d_6$ of steps (i) and (ii).

2. A method for producing MMA-$d_8$ according to claim 1, wherein the step (i) comprises sub-steps of:
   reacting the methanol-$d_4$ with an acid compound to prepare acid methyl-$d_3$-ester which the methyl group is fully deuterated, and
   hydrolyzing the obtained acid methyl-$d_3$-ester with normal water to prepare the $CD_3OH$ and the acid compound.

3. A method for producing MMA-$d_8$ according to claim 1, wherein the step (i) comprises sub-steps of:
   reacting the methanol-$d_4$ and metal to prepare metal methoxide-$d_3$ which methyl group is fully deuterated, and
   hydrolyzing the obtained metal methoxide-$d_3$ with normal water to prepare the $CD_3OH$ end metal hydroxide.

4. A meted for producing MMA-$d_8$ according to claim 1, in which the reutilized deuterium-containing compound to be reutilized in the step (iv) is deuterated water or deuterium atom.

5. A method for producing MMA-$d_8$ according to claim 2, in which the deuterium-containing compound to be reutilized in the step (iv) is a deuterium atom, which is recovered as a deuterium-containing compound when the acid methyl-$d_3$-ester is prepared in the step (i).

6. A method for producing MMA-$d_8$ according to claim 3, in which the deuterium-containing compound to be reutilized in the step (iv) is a deuterium atom, which is recovered as a deuterium-containing compound when the metal methoxide-$d_3$ is prepared in the step (i).

7. A method for producing MMA-$d_8$ according to claim 2, comprising a sub step of reutilizing the acid compound, which is prepared in hydrolyzing the acid methyl-$d_3$-ester in the step (i), as an esterification agent of the methanol-$d_4$ in the step (i).

8. A method for producing MMA-$d_8$ according to claim 1, wherein, when the deuterium-containing compound is recovered to be reutilized in the step (iv), the deuterium-containing compound is present in at least one of:
   (x) a mixture of normal water and deuterated water,
   (y) a deuterium-containing gas and
   (z) water containing deuterium atom.

9. A method for producing MMA-$d_8$ according to claim 8, wherein deuterated water is produced by isotope enrichment from the water which includes deuterium atoms for reutilizing.

10. A method for producing MMA-$d_8$ according to claim 1, wherein the reaction for preparing the acetone cyanohydrin-$d_6$ of the step (ii) is conducted at −20 to 30° C.

* * * * *